United States Patent
Fano et al.

(10) Patent No.: US 9,528,100 B2
(45) Date of Patent: *Dec. 27, 2016

(54) SUBTILASE VARIANTS

(71) Applicant: Novozymes A/S, Bagsvaerd (DK)

(72) Inventors: Tina Sejersgard Fano, Gentofte (DK); Claus Von Der Osten, Lyngby (DK); Malene Kappen Kruger, Kokkedal (DK); Mads Norregaard-Madsen, Birkerod (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/502,234

(22) Filed: Sep. 30, 2014

(65) Prior Publication Data

US 2015/0024990 A1 Jan. 22, 2015

Related U.S. Application Data

(63) Continuation of application No. 14/035,241, filed on Sep. 24, 2013, now abandoned, which is a continuation
(Continued)

(30) Foreign Application Priority Data

Jul. 12, 2001 (DK) .................. 2001 01090

(51) Int. Cl.
*C12N 9/54* (2006.01)
*C11D 3/386* (2006.01)
(Continued)

(52) U.S. Cl.
CPC ............ *C12N 9/54* (2013.01); *C11D 3/38609* (2013.01); *C11D 3/38618* (2013.01);
(Continued)

(58) Field of Classification Search
None
See application file for complete search history.

(56) References Cited

U.S. PATENT DOCUMENTS 4,142,999 A * 3/1979 Bloching ........... C11D 3/38663
435/188
5,155,033 A 10/1992 Estell et al.
(Continued)

FOREIGN PATENT DOCUMENTS

EP 0 251 446 * 12/1994 ............. C12N 15/00
EP 0 675 196 10/1995
(Continued)

OTHER PUBLICATIONS

Kaneko, R., et al., 1989, "Molecular cloning of the structural gene for alkaline elastase YaB, a new subtilisin produced by an alkalophilic Bacillus strain", Journal of Bacteriology, vol. 171, pp. 5232-5236.*

(Continued)

*Primary Examiner* — Nashaat Nashed
*Assistant Examiner* — William W Moore
(74) *Attorney, Agent, or Firm* — Elias Lambiris

(57) ABSTRACT

The present invention relates to novel subtilase variants exhibiting alterations relative to the parent subtilase in one or more properties including: Wash performance, thermal stability, storage stability or catalytic activity. The variants of the invention are suitable for use in e.g. cleaning or detergent compositions, such as laundry detergent compositions and dishwash compositions, including automatic dishwash compositions.

17 Claims, 1 Drawing Sheet

```
No: 1        10        20        30        40        50
a)   AQSVPYGVSQIKAPALHSQGYTGSNVKVAVIDSGIDSSHPDLKVAGGASM
b)   AQSVPWGISRVQAPAAHNRGLTGSGVKVAVLDTGI*STHPDLNIRGGASF

No:        60        70        80        90       100
a)   VPSETNPFQDNNSHGTHVAGTVAALNNSIGVLGVAPSASLYAVKVLGADG
b)   VPGEPST*QDGNGHGTHVAGTIAALNNSIGVLGVAPSAELYAVKVLGASG

No:       110       120       130       140       150
a)   SGQYSWIINGIEWAIANNMDVINMSLGGPSGSAALKAAVDKAVASGVVVV
b)   SGSVSSIAQGLEWAGNNGMHVANLSLGSPSPSATLEQAVNSATSRGVLVV

No:       160       170       180       190       200
a)   AAAGNEGTSGSSSTVGYPGKYPSVIAVGAVDSSNQRASFSSVGPELDVMA
b)   AASGNSG*AGS***ISYPARYANAMAVGATDQNNNRASFSQYGAGLDIVA

No:       210       220       230       240       250
a)   PGVSIQSTLPGNKYGAYNGTSMASPHVAGAAALILSKHPNWTNTQVRSSL
b)   PGVNVQSTYPGSTYASLNGTSMATPHVAGAAALVKQKNPSWSNVQIRNHL

No:       260       270 275
a)   ENTTTKLGDSFYYGKGLINVQAAAQ    (SEQ ID NO.3)
b)   KNTATSLGSTNLYGSGLVNAEAATR    (SEQ ID NO.4)
```

Related U.S. Application Data of application No. 13/872,191, filed on Apr. 29, 2013, now Pat. No. 8,569,035, which is a continuation of application No. 13/038,717, filed on Mar. 2, 2011, now abandoned, which is a continuation of application No. 12/035,766, filed on Feb. 22, 2008, now abandoned, which is a continuation of application No. 10/481,723, filed as application No. PCT/DK02/00485 on Jul. 11, 2002, now abandoned.

(60) Provisional application No. 60/307,242, filed on Jul. 23, 2001.

(51) Int. Cl.
*C12N 9/50* (2006.01)
*C12N 9/52* (2006.01)

(52) U.S. Cl.
CPC ...... *C11D 3/38627* (2013.01); *C11D 3/38636* (2013.01); *C11D 3/38645* (2013.01); *C11D 3/38654* (2013.01); *C12N 9/50* (2013.01); *C12N 9/52* (2013.01); *C12Y 304/21062* (2013.01)

(56) References Cited

U.S. PATENT DOCUMENTS

| | | |
|---|---|---|
| 5,324,653 A | 6/1994 | Van Eekelen et al. |
| 5,336,611 A | 8/1994 | Van Eekelen et al. |
| 5,340,735 A | 8/1994 | Christianson et al. |
| 5,665,587 A | 9/1997 | Aaslyng et al. |
| 5,700,676 A | 12/1997 | Bott et al. |
| 5,741,694 A | 4/1998 | Hastrup et al. |
| 5,846,802 A | 12/1998 | Buxton et al. |
| 6,190,900 B1 | 2/2001 | Sierkstra et al. |
| 6,197,567 B1 | 3/2001 | Aaslyng et al. |
| 6,287,841 B1 | 9/2001 | Mulleners et al. |
| 6,300,116 B1 | 10/2001 | Von der Osten et al. |
| 6,312,936 B1 | 11/2001 | Poulose et al. |
| 6,376,450 B1 | 4/2002 | Ghosh et al. |
| 6,482,628 B1 | 11/2002 | Poulose et al. |
| 6,586,223 B1 | 7/2003 | Sikorski et al. |
| 6,586,224 B1 | 7/2003 | Rubingh et al. |
| 6,599,730 B1 | 7/2003 | Brode et al. |
| 6,610,642 B2 | 8/2003 | Ghosh et al. |
| 6,673,590 B1 | 1/2004 | Poulose et al. |
| 6,773,907 B2 | 8/2004 | Hansen et al. |
| 6,808,913 B2 | 10/2004 | Hastrup et al. |
| 6,815,193 B2 | 11/2004 | Poulose et al. |
| 6,831,053 B1 | 12/2004 | Ghosh et al. |
| 6,838,425 B2 | 1/2005 | Ghosh et al. |
| 6,893,855 B2 | 5/2005 | Norregaard-Madsen |
| 6,902,922 B2* | 6/2005 | Ness .................. C12N 9/6408 435/219 |
| 6,927,055 B2 | 8/2005 | Poulose et al. |
| 7,189,553 B2 | 3/2007 | Aaslyng et al. |
| 7,888,093 B2 | 2/2011 | Draborg et al. |
| 8,569,035 B2* | 10/2013 | Fano ..................... C12N 9/50 435/221 |
| 2002/0128167 A1* | 9/2002 | Ghosh ................. C11D 3/386 510/392 |
| 2004/0180386 A1 | 9/2004 | Carr et al. |
| 2005/0054843 A1 | 3/2005 | Estell et al. |
| 2005/0111461 A1 | 5/2005 | Khan et al. |
| 2005/0148059 A1* | 7/2005 | Estell ..................... A61K 8/66 435/221 |
| 2005/0181446 A1* | 8/2005 | Roggen ................. A21D 2/267 435/7.1 |
| 2006/0228791 A1 | 10/2006 | Roggen et al. |
| 2010/0120091 A1 | 5/2010 | Draborg et al. |
| 2011/0092408 A1 | 4/2011 | Draborg et al. |
| 2012/0149624 A1 | 6/2012 | Draborg et al. |

FOREIGN PATENT DOCUMENTS

| | | |
|---|---|---|
| WO | WO/89/06279 | 7/1989 |
| WO | WO/91/00335 | 1/1991 |
| WO | WO/91/00345 | 1/1991 |
| WO | WO/95/10615 | 4/1995 |
| WO | WO/95/30010 | 11/1995 |
| WO | WO/95/30011 | 11/1995 |
| WO | WO/96/28556 | 9/1996 |
| WO | WO/98/06279 | 2/1998 |
| WO | WO/98/20116 | 5/1998 |
| WO | WO/99/20726 | 4/1999 |
| WO | WO/99/20770 | 4/1999 |
| WO | WO/9920771 | 4/1999 |
| WO | WO/99/27082 | 6/1999 |
| WO | WO/ 01/44452 | 6/2001 |

OTHER PUBLICATIONS

Van der Laan, J.C., et al., 1991, "Cloning, characterization, and multiple chromosomal integration of a Bacillus alkaline protease gene", Applied and Environmental Microbiology, vol. 57, pp. 901-909.*

MacIver, B., et al., 1994, "Cloning and sequencing of a serine proteinase gene from a thermophilic Bacillus species and itsexpression in *Escherichia coli*", Applied and Environmental Microbiology, vol. 60, pp. 3981-3988.*

Takami, H., et al., 2000, "Complete genome sequence of the alkaliphilic bacterium Bacillus halodurans and genomic sequence comparison with Bacillus subtilis", Nucleic Acids Research, vol. 28, pp. 4317-4331.*

Masui et al, Applied and Environmental Microbiology, vol. 60, No. 10, pp. 3579-3584 (1994).

Schmidt et al., Applied and Environmental Microbiology, vol. 61, No. 12, pp. 4490-4493 (1995).

Siezen et al Prot Eng, vol. 4, No. (7, pp. 719-737 (1991).

Takami et al, Appl Microbiol Biotechnol, vol. 38, pp. 101-108 (1992).

Experimental Report showing "Miniwash" tests on BLSAVI variants, which was submitted by Novozymes in the opposition against EP 1409659 as reference D8 (2011).

Corrected Figure 1 of WO 2003/006602, which was submitted by Novozymes in the opposition against EP 1409659 as reference D10 (2011).

Bryan et al., Biochimica et Biophyica Acta, vol. 1543, pp. 203-222 (2000).

Graycar et al., Annals New York Academy of Sciences, vol. 672, pp. 71-79 (1992).

\* cited by examiner

```
No:   1         10        20        30        40        50
a)    AQSVPYGVSQIKAPALHSQGYTGSNVKVAVIDSGIDSSHPDLKVAGGASM
b)    AQSVPWGISRVQAPAAHNRGLTGSGVKVAVLDTGI*STHPDLNIRGGASF

No:             60        70        80        90        100
a)    VPSETNPFQDNNSHGTHVAGTVAALNNSIGVLGVAPSASLYAVKVLGADG
b)    VPGEPST*QDGNGHGTHVAGTIAALNNSIGVLGVAPSAELYAVKVLGASG

No:             110       120       130       140       150
a)    SGQYSWIINGIEWAIANNMDVINMSLGGPSGSAALKAAVDKAVASGVVVV
b)    SGSVSSIAQGLEWAGNNGMHVANLSLGSPSPSATLEQAVNSATSRGVLVV

No:             160       170       180       190       200
a)    AAAGNEGTSGSSSTVGYPGKYPSVIAVGAVDSSNQRASFSSVGPELDVMA
b)    AASGNSG*AGS***ISYPARYANAMAVGATDQNNNRASFSQYGAGLDIVA

No:             210       220       230       240       250
a)    PGVSIQSTLPGNKYGAYNGTSMASPHVAGAAALILSKHPNWTNTQVRSSL
b)    PGVNVQSTYPGSTYASLNGTSMATPHVAGAAALVKQKNPSWSNVQIRNHL

No:             260       270  275
a)    ENTTTKLGDSFYYGKGLINVQAAAQ     (SEQ ID NO.3)
b)    KNTATSLGSTNLYGSGLVNAEAATR     (SEQ ID NO.4)
```

SUBTILASE VARIANTS

CROSS-REFERENCE TO RELATED APPLICATIONS

This application is a continuation of U.S. application Ser. No. 14/035,241 filed on Sep. 24, 2013 (now abandoned), which is a continuation of U.S. application Ser. No. 13/872,191 filed on Apr. 29, 2013 (U.S. Pat. No. 8,569,035), which is a continuation of U.S. application Ser. No. 13/038,717 filed on Mar. 2, 2011 (now abandoned), which is a continuation of U.S. application Ser. No. 12/035,766 filed on Feb. 22, 2008 (now abandoned), which is a continuation of U.S. application Ser. No. 10/481,723 filed Dec. 22, 2003 (now abandoned), which is a 35 U.S.C. 371 national application of PCT/DK02/00485 filed Jul. 11, 2002, which claims priority or the benefit under 35 U.S.C. 119 of Danish application no. PA 2001 01090 filed Jul. 12, 2001 and U.S. Provisional Application No. 60/307,242 filed Jul. 23, 2001, the contents of which are fully incorporated herein by reference.

TECHNICAL FIELD

The present invention relates to novel subtilase variants exhibiting alterations relative to the parent subtilase in one or more properties including: Wash performance, thermal stability, storage stability or catalytic activity. The variants of the invention are suitable for use in e.g. cleaning or detergent compositions, such as laundry detergent compositions and dish wash compositions, including automatic dish wash compositions. The present invention also relates to isolated DNA sequences encoding the variants, expression vectors, host cells, and methods for producing and using the variants of the invention. Further, the present invention relates to cleaning and detergent compositions comprising the variants of the invention.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important enzymes are proteases.

An increasing number of commercially used proteases are protein engineered variants of naturally occurring wild type proteases, e.g. DURAZYM® (Novo Nordisk A/S), RELASE® (Novo Nordisk A/S), MAXAPEM® (Gist-Brocades N.V.), PURAFECT® (Genencor International, Inc.).

Further, a number of protease variants are described in the art. A thorough list of prior art protease variants is given in WO 99/27082.

However, even though a number of useful protease variants have been described, there is still a need for new improved proteases or protease variants for a number of industrial uses such as laundry or hard surface cleaning.

Therefore, an object of the present invention is to provide improved subtilase variants for such purposes.

SUMMARY OF THE INVENTION

Thus, in a first aspect the present invention relates to a subtilase variant comprising at least one or more of the following alterations:
X11{A,R,N,D,C,Q,E,G,H,I,L,K,M,F,S,T,W,Y,V}, deletion, insertion;
X30{A,R,N,D,C,Q,E,G,H,I,L,K,M,F,P,S,T,W,Y,V}, deletion, insertion;
X31{R,N,D,Q,E,H,K,M,P,W,Y}, deletion, insertion;
X32{A,R,D,C,E,G,H,I,L,K,M,F,P,T,W,Y,V}, insertion;
X34{A,R,N,D,C,Q,E,G,H,I,L,K,M,F,S,T,W,Y,V}, deletion;
X65{A,R,C,G,H,I,L,K,M,F,T,W,Y,V}, deletion, insertion;
X66{A,R,C,H,I,L,K,M,F,T,W,Y,V}, deletion, insertion;
X67{A,R,N,Q,G,H,I,K,M,F,P,S,T,W,Y,V};
X68{R,N,D,Q,E,G,H,I,L,K,F,P,S,T,W,Y,V}, deletion, insertion;
X69{A,R,N,D,Q,E,G,H,I,L,K,M,F,P,S,T,W,Y,V}, deletion, insertion;
X70G;
X71T;
X77N;
X83G, insertion;
X84V;
X85{A,R,N,D,Q,E,G,H,I,L,M,F,S,T,W,Y,V};
X90{A,R,N,D,C,Q,E,G,H,I,L,K,M,F,P,S,T,W,Y,V}, deletion, insertion;
X95{R,K,F,W,Y,V}, deletion;
X107I
X110G, insertion;
X121V, insertion;
X122 insertion;
X123N;
X125S;
X150{A,R,N,D,Q,E,G,H,I,L,K,M,F,P,S,T,W,Y,V}, deletion, insertion;
X152{A,R,N,D,Q,E,H,K,F,P,W,Y,V};
X153{R,N,D,Q,E,G,H,I,L,K,M,F,T,W,Y,V};
X154{A,R,G,H,I,L,M,F,W,Y,V};
X164{A,R,H,T,W};
X165{R,L,F,W,Y};
X166{W,Y}, insertion;
X175{R,N,D,Q,E,G,H,K,M,F,P,T,W,Y,V};
X177{R,N,D,Q,E,G,H,I,L,K,M,F,P,S,T,W,Y,V}, deletion, insertion;
X178{A,R,N,D,C,Q,E,G,H,I,L,K,M,F,P,S,T,W,Y,V}, deletion, insertion;
X180{A,R,N,D,C,Q,E,G,H,I,L,K,M,F,P,S,T,W,Y,V}, deletion, insertion;
X199{R,L,K,F,W,Y,V}, deletion, insertion;
X200{A,R,I,L,K,M,F,W,Y,V}, deletion, insertion;
X201{A,R,H,I,L,K,M,F,P,T,W,Y,V}, deletion, insertion;
X202{A,R,C,G,H,I,L,K,M,F,T,W,Y,V};
X207{A,R,N,C,Q,G,H,I,L,K,M,F,P,S,T,W,Y,V};
X220T, insertion;
X223A, insertion;
X225P, insertion;
X226H, insertion;
X227V, insertion;
X228A, insertion;
X229G, insertion;
X230 insertion;
X231A, insertion;
X253{A,R,N,D,Q,E,G,H,I,L,M,F,S,T,W,Y,V}, deletion, insertion;
X264{A,R,N,Q,G,H,I,L,M,F,S,T,W,Y,V}, deletion, insertion;
X266{A,R,N,D,C,Q,E,G,H,I,L,K,M,F,S,T,W,Y,V}, deletion, insertion; wherein
(a) the alteration(s) are independently, as specified,
   (i) a substitution of the amino acid, which occupies the position with a different amino acid,
   (ii) a deletion of the amino acid which occupies the position, or (iii) an insertion of at least one additional amino acid, which occupies the position,
(b) the variant has protease activity, and
(c) each position corresponds to a position of the amino acid sequence of subtilisin BPN', shown in FIG. 1 (SEQ ID NO:3).

In a second aspect the present invention relates to an isolated polynucleotide encoding a subtilase variant of the invention.

In a third aspect the present invention relates to an expression vector comprising the isolated polynucleotide of the invention.

In a fourth aspect the present invention relates to a microbial host cell transformed with the expression vector of the invention.

In a fifth aspect the present invention relates to a method for producing a subtilase variant according to the invention, wherein a host according to the invention is cultured under conditions conducive to the expression and secretion of the variant, and the variant is recovered.

In an sixth aspect the present invention relates to a cleaning or detergent composition, preferably a laundry or dish wash composition, comprising the variant of the invention.

Concerning alignment and numbering, reference is made to FIG. 1 which shows an alignments between subtilisin BPN'(a) (BASBPN) (SEQ ID NO:3) and subtilisin 309 (BLSAVI)(b) (SEQ ID NO:4).

This alignment is in this patent application used as a reference for numbering the residues.

DEFINITIONS

Prior to discussing this invention in further detail, the following terms and conventions will first be defined.

| NOMENCLATURE OF AMINO ACIDS | | |
| --- | --- | --- |
| A = | Ala = | Alanine |
| V = | Val = | Valine |
| L = | Leu = | Leucine |
| I = | Ile = | Isoleucine |
| P = | Pro = | Proline |
| F = | Phe = | Phenylalanine |
| W = | Trp = | Tryptophan |
| M = | Met = | Methionine |
| G = | Gly = | Glycine |
| S = | Ser = | Serine |
| T = | Thr = | Threonine |
| C = | Cys = | Cysteine |
| Y = | Tyr = | Tyrosine |
| N = | Asn = | Asparagine |
| Q = | Gln = | Glutamine |
| D = | Asp = | Aspartic Acid |
| E = | Glu = | Glutamic Acid |
| K = | Lys = | Lysine |
| R = | Arg = | Arginine |
| H = | His = | Histidine |
| X = | Xaa = | Any amino acid |

| NOMENCLATURE OF NUCLEIC ACIDS | |
| --- | --- |
| A = | Adenine |
| G = | Guanine |
| C = | Cytosine |
| T = | Thymine (only in DNA) |
| U = | Uracil (only in RNA) |

Nomenclature and Conventions for Designation of Variants

In describing the various subtilase enzyme variants produced or contemplated according to the invention, the following nomenclatures and conventions have been adapted for ease of reference:

A frame of reference is first defined by aligning the isolated or parent enzyme with subtilisin BPN' (BASBPN).

The alignment can be obtained by the GAP routine of the GCG package version 9.1 to number the variants using the following parameters: gap creation penalty=8 and gap extension penalty=8 and all other parameters kept at their default values.

Another method is to use known recognized alignments between subtilases, such as the alignment indicated in WO 91/00345. In most cases the differences will not be of any importance.

Thereby a number of deletions and insertions will be defined in relation to BASBPN (SEQ ID NO. 3). In FIG. 1, subtilisin 309 (SEQ ID NO. 4) has 6 deletions in positions 36, 58, 158, 162, 163, and 164 in comparison to BASBPN. These deletions are in FIG. 1 indicated by asterixes (*).

The various modifications performed in a parent enzyme is indicated in general using three elements as follows:
Original Amino Acid Position Substituted Amino Acid The notation G195E thus means a substitution of a glycine in position 195 with a glutamic acid.

In the case where the original amino acid residue may be any amino acid residue, a short hand notation may at times be used indicating only the position and substituted amino acid:
Position Substituted Amino Acid Such a notation is particular relevant in connection with modification(s) in homologous subtilases (vide infra).

Similarly when the identity of the substituting amino acid residue(s) is immaterial:
Original Amino Acid Position When both the original amino acid(s) and substituted amino acid(s) may comprise any amino acid, then only the position is indicated, e.g.: 170.

When the original amino acid(s) and/or substituted amino acid(s) may comprise more than one, but not all amino acid(s), then the selected amino acids are indicated inside brackets:
Original Amino Acid Position {Substituted Amino Acid$_1$, . . . , Substituted Amino Acid$_n$}

For specific variants the specific three or one letter codes are used, including the codes Xaa and X to indicate any amino acid residue.
Substitutions:

The substitution of glutamic acid for glycine in position 195 is designated as:
 Gly195Glu or G195E
or the substitution of any amino acid residue acid for glycine in position 195 is designated as:
 Gly195Xaa or G195X
or
 Gly195 or G195

The substitution of serine for any amino acid residue in position 170 would thus be designated
 Xaa170Ser or X170S.
or
 170Ser or 170S Such a notation is particular relevant in connection with modification(s) in homologous subtilases (vide infra). 170Ser is thus meant to comprise e.g. both a Lys170Ser modification in BASBPN and Arg170Ser modification in BLSAVI (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by Arg170{Gly,Ala,Ser,Thr} or R170{G,A,S,T} to indicate the variants

R170G, R170A, R170S, and R170T.

Deletions:

A deletion of glycine in position 195 will be indicated by:

Gly195* or G195*

Correspondingly the deletion of more than one amino acid residue, such as the deletion of glycine and leucine in positions 195 and 196 will be designated Gly195*+Leu196*or G195*+L196*

Insertions:

The insertion of an additional amino acid residue such as e.g. a lysine after G195 is indicated by:

Gly195GlyLys or G195GK;

or, when more than one amino acid residue is inserted, such as e.g. a Lys and Ala after G195 this will be indicated as:

Gly195GlyLysAla or G195GKA

In such cases the inserted amino acid residue(s) are numbered by the addition of lower case letters to the position number of the amino acid residue preceding the inserted amino acid residue(s). In the above example the sequences 194 to 196 would thus be:

```
                         (SEQ ID NO. 1)
              194 195 196
    BLSAVI     A - G - L
              194 195 195a 195b 196
    Variant    A - G - K  - A  - L
```

In cases where an amino acid residue identical to the existing amino acid residue is inserted it is clear that degeneracy in the nomenclature arises. If for example a glycine is inserted after the glycine in the above example this would be indicated by G195GG. The same actual change could just as well be indicated as A194AG for the change from

```
                         (SEQ ID NO. 2)
              194 195 196
    BLSAVI     A - G - L
    to
              194 195 195a 196
    Variant    A - G - G  - L
              194 194a 195 196
```

Such instances will be apparent to the skilled person, and the indication G195GG and corresponding indications for this type of insertions are thus meant to comprise such equivalent degenerate indications.

Filling a Gap:

Where a deletion in an enzyme exists in the reference comparison with the subtilisin BPN' sequence used for the numbering, an insertion in such a position is indicated as:

*36Asp or *36D for the insertion of an aspartic acid in position 36

Multiple Modifications:

Variants comprising multiple modifications are separated by pluses, e.g.:

Arg170Tyr+Gly195Glu or R170Y+G195E representing modifications in positions 170 and 195 substituting tyrosine and glutamic acid for arginine and glycine, respectively.

Thus, Tyr167{Gly,Ala,Ser,Thr}+Arg170{Gly,Ala,Ser,Thr} designates the following variants:

Tyr167Gly+Arg170Gly, Tyr167Gly+Arg170Ala,
Tyr167Gly+Arg170Ser, Tyr167Gly+Arg170Thr,
Tyr167Ala+Arg170Gly, Tyr167Ala+Arg170Ala,
Tyr167Ala+Arg170Ser, Tyr167Ala+Arg170Thr,
Tyr167Ser+Arg170Gly, Tyr167Ser+Arg170Ala,
Tyr167Ser+Arg170Ser, Tyr167Ser+Arg170Thr,
Tyr167Thr+Arg170Gly, Tyr167Thr+Arg170Ala,
Tyr167Thr+Arg170Ser, and Tyr167Thr+Arg170Thr.

This nomenclature is particular relevant relating to modifications aimed at substituting, replacing, inserting or deleting amino acid residues having specific common properties, such as residues of positive charge (K, R, H), negative charge (D, E), or conservative amino acid modification(s) of e.g.

Tyr167{Gly,Ala,Ser,Thr}+Arg170{Gly,Ala,Ser,Thr}, which signifies substituting a small amino acid for another small amino acid. See section "Detailed description of the invention" for further details.

Proteases

Enzymes cleaving the amide linkages in protein substrates are classified as proteases, or (interchangeably) peptidases (see Walsh, 1979, Enzymatic Reaction Mechanisms. W.H. Freeman and Company, San Francisco, Chapter 3).

Numbering of Amino Acid Positions/Residues

If nothing else is mentioned the amino acid numbering used herein correspond to that of the subtilase BPN' (BASBPN) sequence. For further description of the BPN' sequence, see FIG. 1 or Siezen et al., *Protein Engng.* 4 (1991) 719-737.

Serine Proteases

A serine protease is an enzyme which catalyzes the hydrolysis of peptide bonds, and in which there is an essential serine residue at the active site (White, Handler and Smith, 1973 "*Principles of Biochemistry*," Fifth Edition, McGraw-Hill Book Company, NY, pp. 271-272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41 711-753).

Subtilases

A sub-group of the serine proteases tentatively designated subtilases has been proposed by Siezen et al., *Protein Engng.* 4 (1991) 719-737 and Siezen et al. *Protein Science* 6 (1997) 501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true" subtilisins, comprises the "classical" subtilisins, such as subtilisin 168 (BSS168), subtilisin BPN', subtilisin Carlsberg (ALCALASE®, NOVOZYMES A/S), and subtilisin DY (BSSDY).

A further subgroup of the subtilases, I-S2 or high alkaline subtilisins, is recognized by Siezen et al. (supra). Sub-group I-S2 proteases are described as highly alkaline subtilisins and comprises enzymes such as subtilisin PB92 (BAALKP) (MAXACAL®, Gist-Brocades NV), subtilisin 309 (SAVINASE®, NOVOZYMES A/S), subtilisin 147 (BLS147) (ESPERASE®, NOVOZYMES A/S), and alkaline elastase YaB (BSEYAB).

"SAVINASE®"

SAVINASE® is marketed by NOVOZYMES NS. It is subtilisin 309 from *B. Lentus* and differs from BAALKP only in one position (N87S, see FIG. 1 herein). SAVINASE® has the amino acid sequence designated b) in FIG. 1.

Parent Subtilase

The term "parent subtilase" describes a subtilase defined according to Siezen et al. (1991 and 1997). For further details see description of "SUBTILASES" immediately above. A parent subtilase may also be a subtilase isolated from a natural source, wherein subsequent modifications have been made while retaining the characteristic of a subtilase. Furthermore, a parent subtilase may also be a subtilase which has been prepared by the DNA shuffling technique, such as described by J. E. Ness et al., Nature Biotechnology, 17, 893-896 (1999). Alternatively the term "parent subtilase" may be termed "wild type subtilase".

For reference a table of the acronyms for various subtilases mentioned herein is provided, for further acronyms, see Siezen et al., *Protein Engng.* 4 (1991) 719-737 and Siezen et al. *Protein Science* 6 (1997) 501-523.

TABLE I

| Organism Bacteria: Gram-positive | enzyme | acronym |
|---|---|---|
| Bacillus subtilis 168 | subtilisin I168, apr | BSS168 |
| Bacillus amyloliquefaciens | subtilisin BPN'(NOVO) | BASBPN |
| Bacillus subtilis DY | subtilisin DY | BSSDY |
| Bacillus licheniformis | subtilisin Carlsberg | BLSCAR |
| Bacillus lentus | subtilisin 309 | BLSAVI |
| Bacillus lentus | subtilisin 147 | BLS147 |
| Bacillus alcalophilus PB92 | subtilisin PB92 | BAPB92 |
| Bacillus YaB | alkaline elastase YaB | BYSYAB |
| Thermoactinomyces vulgaris | thermitase | TVTHER |

Modification(s) of a Subtilase Variant

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host.

Homologous Subtilase Sequences

The homology between two amino acid sequences is in this context described by the parameter "identity".

In order to determine the degree of identity between two subtilases the GAP routine of the GCG package version 9.1 can be applied (infra) using the same settings. The output from the routine is besides the amino acid alignment the calculation of the "Percent Identity" between the two sequences.

Based on this description it is routine for a person skilled in the art to identify suitable homologous subtilases, which can be modified according to the invention.

Isolated Polynucleotide

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985). The term "an isolated polynucleotide" may alternatively be termed "a cloned polynucleotide".

Isolated Protein

When applied to a protein, the term "isolated" indicates that the protein has been removed from its native environment.

In a preferred form, the isolated protein is substantially free of other proteins, particularly other homologous proteins (i.e. "homologous impurities" (see below)).

An isolated protein is more than 10% pure, preferably more than 20% pure, more preferably more than 30% pure, as determined by SDS-PAGE. Further it is preferred to provide the protein in a highly purified form, i.e., more than 40% pure, more than 60% pure, more than 80% pure, more preferably more than 95% pure, and most preferably more than 99% pure, as determined by SDS-PAGE.

The term "isolated protein" may alternatively be termed "purified protein".

Homologous Impurities

The term "homologous impurities" means any impurity (e.g. another polypeptide than the subtilase of the invention), which originate from the homologous cell where the subtilase of the invention is originally obtained from.

Obtained from

The term "obtained from" as used herein in connection with a specific microbial source, means that the polynucleotide and/or subtilase produced by the specific source, or by a cell in which a gene from the source has been inserted.

Substrate

The term "substrate" used in connection with a substrate for a protease should be interpreted in its broadest form as comprising a compound containing at least one peptide (amide) bond susceptible to hydrolysis by a subtilisin protease.

Product

The term "product" used in connection with a product derived from a protease enzymatic reaction should, in the context of the present invention, be interpreted to include the products of a hydrolysis reaction involving a subtilase protease. A product may be the substrate in a subsequent hydrolysis reaction.

Wash Performance

In the present context the term "wash performance" is used as an enzyme's ability to remove proteinaceous or organic stains present on the object to be cleaned during e.g. wash or hard surface cleaning. See also the "Model Detergent Wash Performance Test" in Example 3 herein.

Performance Factor

The term "Performance Factor" is defined with respect to the below formula $$P = R_{variant} - R_{parent}$$

wherein P is the Performance Factor, $R_{variant}$ is the reflectance (measured at 460 nm) of the test material after being treated with a subtilase variant as described in the "Model Detergent Wash Performance Test", and $R_{parent}$ is the reflectance (measured at 460 nm) of the test material after being treated with the corresponding parent subtilase as described in the "Model Detergent Wash Performance Test". For further details, see the "Model Detergent Wash Performance Test" in Example 3 herein.

BRIEF DESCRIPTION OF THE DRAWING

FIG. 1 shows an alignment between subtilisin BPN' (a) (SEQ ID NO:3) and Savinase® (b) (SEQ ID NO:4) using the GAP routine mentioned above.

DETAILED DESCRIPTION OF THE INVENTION

The present invention relates to novel subtilase variants exhibiting alterations relative to the parent subtilase in one or more properties including: Wash performance, thermal stability, storage stability or catalytic activity.

Variants which are contemplated as being part of the invention are such variants where, when compared to the wild-type subtilase, one or more amino acid residues has been substituted, deleted or inserted in at least one or more of the following positions:
11, 30, 31, 32, 34, 65, 66, 67, 68, 69, 70, 71, 77, 83, 84, 85, 90, 95, 107, 110, 121, 122, 123, 125, 150, 152, 153, 154, 164, 165, 166, 175, 177, 178, 180, 199, 200, 201, 202, 207, 220, 223, 225, 226, 227, 228, 229, 230, 231, 253, 264 or 266 (BASBPN numbering).

In the Savinase® sequence (SEQ ID NO:4) shown in FIG. 1, the positions to be mutated are one or more of:
V11, V30, L31, D32, G34, G65, T66, H67, V68, A69, G70, T71, N77, G83, V84, A85, L90, V95, I107, G110, V121, A122, N123, S125, V150, A152, S153, G154, *164, *165, *166, M175, V177, G178, T180, V199, A200, P201, G202, S207, T220, A223, P225, H226, V227, A228, G229, A230, A231, T253, G264 or G266.

Specific substitutions/deletions/insertions contemplated are:
X11{A,R,N,D,C,Q,E,G,H,I,L,K,M,F,S,T,W,Y,V}, deletion, insertion;
X30{A,R,N,D,C,Q,E,G,H,I,L,K,M,F,P,S,T,W,Y,V}, deletion, insertion;
X31{R,N,D,Q,E,H,K,M,P,W,Y}, deletion, insertion;
X32{A,R,D,C,E,G,H,I,L,K,M,F,P,T,W,Y,V}, insertion;
X34{A,R,N,D,C,Q,E,G,H,I,L,K,M,F,S,T,W,Y,V}, deletion;
X65{A,R,C,G,H,I,L,K,M,F,T,W,Y,V}, deletion, insertion;
X66{A,R,C,H,I,L,K,M,F,T,W,Y,V}, deletion, insertion;
X67{A,R,N,Q,G,H,I,K,M,F,P,S,T,W,Y,V};
X68{R,N,D,Q,E,G,H,I,L,K,F,P,S,T,W,Y,V}, deletion, insertion;
X69{A,R,N,D,Q,E,G,H,I,L,K,M,F,P,S,T,W,Y,V}, deletion, insertion;
X70G;
X71T;
X77N;
X83G, insertion;
X84V;
X85{A,R,N,D,Q,E,G,H,I,L,M,F,S,T,W,Y,V};
X90{A,R,N,D,C,Q,E,G,H,I,L,K,M,F,P,S,T,W,Y,V}, deletion, insertion;
X95{R,K,F,W,Y,V}, deletion;
X107I
X110G, insertion;
X121V, insertion;
X122 insertion;
X123N;
X125S;
X150{A,R,N,D,Q,E,G,H,I,L,K,M,F,P,S,T,W,Y,V}, deletion, insertion;
X152{A,R,N,D,Q,E,H,K,F,P,W,Y,V};
X153{R,N,D,Q,E,G,H,I,L,K,M,F,T,W,Y,V};
X154{A,R,G,H,I,L,M,F,W,Y,V};
X164{A,R,H,T,W};
X165{R,L,F,W,Y};
X166{W,Y}, insertion;
X175{R,N,D,Q,E,G,H,K,M,F,P,T,W,Y,V};
X177{R,N,D,Q,E,G,H,I,L,K,M,F,P,S,T,W,Y,V}, deletion, insertion;
X178{A,R,N,D,C,Q,E,G,H,I,L,K,M,F,P,S,T,W,Y,V}, deletion, insertion;
X180{A,R,N,D,C,Q,E,G,H,I,L,K,M,F,P,S,T,W,Y,V}, deletion, insertion;
X199{R,L,K,F,W,Y,V}, deletion, insertion;
X200{A,R,I,L,K,M,F,W,Y,V}, deletion, insertion;
X201{A,R,H,I,L,K,M,F,P,T,W,Y,V}, deletion, insertion;
X202{A,R,C,G,H,I,L,K,M,F,T,W,Y,V};
X207{A,R,N,C,Q,G,H,I,L,K,M,F,P,S,T,W,Y,V};
X220T, insertion;
X223A, insertion;
X225P, insertion;
X226H, insertion;
X227V, insertion;
X228A, insertion;
X229G, insertion;
X230 insertion;
X231A, insertion;
X253{A,R,N,D,Q,E,G,H,I,L,M,F,S,T,W,Y,V}, deletion, insertion;
X264{A,R,N,Q,G,H,I,L,M,F,S,T,W,Y,V}, deletion, insertion;
X266{A,R,N,D,C,Q,E,G,H,I,L,K,M,F,S,T,W,Y,V}, deletion, insertion
where each position corresponds to a position in subtilisin BPN' as shown in FIG. 1.

A subtilase variant of the first aspect of the invention may be a parent or wild-type subtilase identified and isolated from nature.

Such a parent wildtype subtilase may be specifically screened for by standard techniques known in the art.

One preferred way of doing this may be by specifically PCR amplify conserved DNA regions of interest from subtilases from numerous different microorganism, preferably different *Bacillus* strains.

Subtilases are a group of conserved enzymes, in the sense that their DNA and amino acid sequences are homologous. Accordingly it is possible to construct relatively specific primers flanking the polynucleotide sequences of interest.

Using such PCR primers to amplify DNA from a number of different microorganisms, preferably different *Bacillus* strains, followed by DNA sequencing of said amplified PCR fragments, it will be possible to identify strains which produce subtilase variants of the invention. Having identified the strain and a partial DNA sequence of such a subtilase of interest, it is routine work for a person skilled in the art to complete cloning, expression and purification of such a subtilase.

However, it is envisaged that a subtilase variant of the invention is predominantly a variant of a parent subtilase.

A subtilase variant suitable for the uses described herein, may be constructed by standard techniques known in the art such as by site-directed/random mutagenesis or by DNA shuffling of different subtilase sequences. See the "Material and Methods" section herein (vide infra) for further details.

As will be acknowledged by the skilled person, the variants described herein may comprise one or more further modifications, in particular one or more further substitutions.

Moreover, the variants described herein may encompass mutation at more than just one position. For example the variant according to the invention may contain mutations at one position, two positions, or more than two positions, such as three, four or five positions.

It is well known in the art that a so-called conservative substitution of one amino acid residue to a similar amino acid residue is expected to produce only a minor change in the characteristic of the enzyme.

Table II below list groups of conservative amino acid substitutions.

TABLE II

Conservative amino acid substitutions

| Common Property | Amino Acid |
|---|---|
| Basic (positive charge) | K = lysine |
|  | H = histidine |
| Acidic (negative charge) | E = glutamic acid |
|  | D = aspartic acid |
| Polar | Q = glutamine |
|  | N = asparagine |
| Hydrophobic | L = leucine |
|  | I = isoleucine |
|  | V = valine |
|  | M = methionine |
| Aromatic | F = phenylalanine |
|  | W = tryptophan |
|  | Y = tyrosine |
| Small | G = glycine |
|  | A = alanine |
|  | S = serine |
|  | T = threonine |

According to this principle subtilase variants comprising conservative substitutions are expected to exhibit characteristics that are not drastically different from each other.

Based on the disclosed and/or exemplified subtilase variants herein, it is routine work for a person skilled in the art to identify suitable conservative modification(s) to these variants in order to obtain other subtilase variants exhibiting similarly improved wash-performance.

It is preferred that the parent subtilase belongs to the subgroups I-S1 and I-S2, especially subgroup I-S2, both for enzymes from nature or from the artificial creation of diversity, and for designing and producing variants from a parent subtilase.

In relation to variants from subgroup I-S1, it is preferred to select a parent subtilase from the group consisting of BSS168 (BSSAS, BSAPRJ, BSAPRN, BMSAMP), BASBPN, BSSDY, BLSCAR (BLKERA, BLSCA1, BLSCA2, BLSCA3), BSSPRC, and BSSPRD, or functional variants thereof having retained the characteristic of subgroup I-S1.

In relation to variants from subgroup I-S2 it is preferred to select a parent subtilase from the group consisting of BSAPRQ, BLS147 (BSAPRM, BAH101), BLSAVI (BSKSMK, BAALKP, BLSUBL), BYSYAB, BAPB92, TVTHER, and BSAPRS, or functional variants thereof having retained the characteristic of sub-group I-S2.

In particular, the parent subtilase is BLSAVI (Savinase®, NOVOZYMES A/S), and a preferred subtilase variant of the invention is accordingly a variant of Savinase®.

The present invention also encompasses any of the above mentioned subtilase variants in combination with any other modification to the amino acid sequence thereof. Especially combinations with other modifications known in the art to provide improved properties to the enzyme are envisaged. The art describes a number of subtilase variants with different improved properties and a number of those are mentioned in the "Background of the invention" section herein (vide supra). Those references are disclosed here as references to identify a subtilase variant, which advantageously can be combined with a subtilase variant described herein.

Such combinations comprise the positions: 222 (improves oxidation stability), 218 (improves thermal stability), substitutions in the $Ca^{2+}$-binding sites stabilizing the enzyme, e.g. position 76, and many other apparent from the prior art.

In further embodiments a subtilase variant described herein may advantageously be combined with one or more modification(s) in any of the positions:
27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274.

Specifically, the following BLSAVI, BLSUBL, BSKSMK, and BAALKP modifications are considered appropriate for combination:
K27R, *36D, S56P, N76D, S87N, G97N, S101G, S103A, V104A, V104I, V104N, V104Y, H120D, N123S, G159D, Y167, R170, Q206E, N218S, M222S, M222A, T224S, A232V, K235L, Q236H, Q245R, N248D, N252K and T274A.

Furthermore variants comprising any of the modifications S101G+V104N, S87N+S101G+V104N, K27R+V104Y+N123S+T274A, N76D+S103A+V104I or N76D+V104A, or other combinations of the modifications K27R, N76D, S101G, S103A, V104N, V104Y, V104I, V104A, N123S, G159D, A232V, Q236H, Q245R, N248D, N252K, T274A in combination with any one or more of the modification(s) mentioned above exhibit improved properties.

A particular interesting variant is a variant, which, in addition to modifications according to the invention, contains the following substitutions:
S101G+S103A+V104I+G159D+A232V+Q236H+Q245R+N248D+N252K.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

Furthermore the following specific variants of the invention are considered interesting:
BPN' (BASBPN):
I11V,L
L90I,V
M199* (deletion)

Savinase (BLSAVI):

V11I; V11I+144V; V11I+L96LA; S9R+V11I+A15T+T22A; V11I+L96LA+A108C+A138C; V11I+N76D+A194P+A230V; V11I+V84I; V11I+V84I+K251R; V11I+V30I; V11I+V139L; V11I+V30I; V30I; V30I+V84I; V30I+V139L; S9R+A15T+T22A+V30I; V30I+V244R; V30I+K251R; V30I+V139L+Y167A+R170S+A194P+N218S; D32A; V68A; V68A+S106A; V68A,+V139I; V68A,+A158V; V68A+V203A; V68A+V139L; A48T+V68A+P131M; V51A+V68A+S106T+A168G; V51A+V68A+S106T+A168G; N76D+M175ML+A194P+A230V; N76D+M175MI+A194P+A230V;

The wash performance of a selected variant of the invention may be tested in the "Model Detergent Wash Performance Test" disclosed in Example 3 herein. The "Model Detergent Wash Performance Test" may be employed to assess the ability of a variant, when incorporated in a standard detergent composition, to remove proteinaceous stains from a standard textile as compared to a reference system, namely the parent subtilase (incorporated in the same model detergent system and tested under identical conditions). Using this test, the wash performance of a selected variant can be initially investigated, the rationale being that if a selected variant does not show a significant improvement in the test compared to the parent subtilase, it is normally not necessary to carry out further test experiments.

Therefore, variants which are particular interesting for the purposes described herein, are such variants which, when tested in a model detergent composition comprising 6.2% LAS (Nansa 80S)
2% Sodium salt of $C_{16}$-$C_{18}$ fatty acid
4% Non-ionic surfactant (Plurafax LF404)
22% Zeolite P
10.5% $Na_2CO_3$
4% $Na_2Si_2O_5$
2% Carboxymethylcellulose (CMC)
6.8% Acrylate liquid CP5 40%
20% Sodium perborate (empirical formula $NaBO_2.H_2O_2$)
0.2% EDTA
21% $Na_2SO_4$
Water (balance)

as described in the "Model Detergent Wash Performance Test" herein, shows an improved wash performance as compared to the parent subtilase tested under identical conditions.

The improvement in the wash performance may be quantified by employing the so-called "Performance Factor" defined in Example 3, herein.

In a very interesting embodiment of the invention, the variant of the invention, when tested in the "Wash Performance Test" has a Performance Factor of at least 1, such as at least 1.5, e.g. at least 2, preferably at least 2.5, such as at least 3, e.g. at least 3.5, in particular at least 4, such as at least 4.5, e.g. at least 5.

Evidently, it is preferred that the variant of the invention fulfils the above criteria on at least the stated lowest level, more preferably at the stated intermediate level and most preferably on the stated highest level.

Producing a Subtilase Variant

Many methods for cloning a subtilase and for introducing substitutions, deletions or insertions into genes (e.g. subtilase genes) are well known in the art.

In general standard procedures for cloning of genes and introducing mutations (random and/or site directed) into said genes may be used in order to obtain a subtilase variant of the invention. For further description of suitable techniques reference is made to Examples herein (vide infra) and (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990), and WO 96/34946.

Further, a subtilase variant may be constructed by standard techniques for artificial creation of diversity, such as by DNA shuffling of different subtilase genes (WO 95/22625; Stemmer WPC, Nature 370:389-91 (1994)). DNA shuffling of e.g. the gene encoding Savinase® with one or more partial subtilase sequences identified in nature, will after subsequent screening for improved wash performance variants, provide subtilase variants suitable for the purposes described herein.

Expression Vectors

A recombinant expression vector comprising a DNA construct encoding the enzyme of the invention may be any vector that may conveniently be subjected to recombinant DNA procedures.

The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid.

Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector.

The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, or strains of *Streptomyces*, such as *S. lividans* or *S. murinus*, or gram-negative bacteria such as *Escherichia coli*.

The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as *Bacillus* or *Streptomyces* strains, the enzyme may be retained in the cytoplasm, or may be directed to the extracellular medium by a bacterial secretion sequence. In the latter case, the enzyme may be recovered from the medium as described below.

Method for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context homologous impurities means any impurities (e.g. other polypeptides than the enzyme of the invention), which originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Cleaning and Detergent Compositions

In general, cleaning and detergent compositions are well described in the art and reference is made to WO 96/34946; WO 97/07202; WO 95/30011 for further description of suitable cleaning and detergent compositions.

Detergent Compositions

The subtilase variant may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising a subtilase enzyme of the invention. The detergent additive as well as the detergent composition may comprise one or more other enzymes such as another protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™ Primase™, Duralase™, Esperase™, and Kannase™ (Novozymes A/S), Maxatase™ Maxacal™, Maxapem™, Properase™, Purafect™, Purafect OxP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases:

Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition typically comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 that is hereby incorporated as reference.

The invention is described in further detail in the following examples, which are not in any way intended to limit the scope of the invention as claimed.

In the detergent compositions, the abbreviated component identifications have the following meanings:
LAS: Sodium linear $C_{12}$ alkyl benzene sulfonate
TAS: Sodium tallow alkyl sulfate
XYAS: Sodium $C_{1X}$-$C_{1Y}$ alkyl sulfate
SS: Secondary soap surfactant of formula 2-butyl octanoic acid
25EY: A $C_{12}$-$C_{15}$ predominantly linear primary alcohol condensed with an average of Y moles of ethylene oxide
45EY: A $C_{14}$-$C_{15}$ predominantly linear primary alcohol condensed with an average of Y moles of ethylene oxide
XYEZS: $C_{1X}$-$C_{1Y}$ sodium alkyl sulfate condensed with an average of Z moles of ethylene oxide per mole
Nonionic: $C_{13}$-$C_{15}$ mixed ethoxylated/propoxylated fatty alcohol with an average degree of ethoxylation of 3.8 and an average degree of propoxylation of 4.5 sold under the trade name Plurafax LF404 by BASF GmbH
CFAA: $C_{12}$-$C_{14}$ alkyl N-methyl glucamide
TFAA: $C_{16}$-$C_{18}$ alkyl N-methyl glucamide
Silicate: Amorphous Sodium Silicate ($SiO_2$:$Na_2O$ ratio=2.0)
NaSKS-6: Crystalline layered silicate of formula $\delta$-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the trade name PA30 by BASF GmbH
Zeolite A: Hydrated Sodium Aluminosilicate of formula $Na_{12}(AlO_2SiO_2)_{12}\cdot 27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2\cdot H_2O_2$
PB4: Anhydrous sodium perborate tetrahydrate
Percarbonate: Anhydrous sodium percarbonate bleach of empirical formula $2Na_2CO_3\cdot 3H_2O_2$
TAED: Tetra-acetyl ethylene diamine
CMC: Sodium carboxymethyl cellulose
DETPMP: Diethylene triamine penta(methylene phosphonic acid), marketed by Monsanto under the Trade name Dequest 2060
PVP: Polyvinylpyrrolidone polymer
EDDS: Ethylene diamine-N, N'-disuccinic acid, [S,S] isomer in the form of the sodium salt
Suds Suppressor: 25% paraffin wax Mpt 50° C., 17% hydrophobic silica, 58% paraffin oil
Granular Suds suppressor: 12% Silicone/silica, 18% stearyl alcohol, 70% starch in granular form
Sulfate: Anhydrous sodium sulfate
HMWPEO: High molecular weight polyethylene oxide
TAE 25: Tallow alcohol ethoxylate (25)

Detergent Example I

A granular fabric cleaning composition in accordance with the invention may be prepared as follows:

| | |
|---|---|
| Sodium linear $C_{12}$ alkyl Benzene sulfonate | 6.5 |
| Sodium sulfate | 15.0 |
| Zeolite A | 26.0 |
| Sodium nitrilotriacetate | 5.0 |
| Enzyme | 0.1 |
| PVP | 0.5 |
| TAED | 3.0 |
| Boric acid | 4.0 |
| Perborate | 18.0 |
| Phenol sulfonate | 0.1 |
| Minors | up to 100% |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |

-continued

| | |
|---|---|
| CMC | 0.4 |
| Enzyme | 0.1 |
| TAED | 6.0 |
| Percarbonate | 22.0 |
| EDDS | 0.3 |
| Granular suds suppressor | 3.5 |
| Water/minors | Up to 100% |

Detergent Example III

Granular fabric cleaning compositions in accordance with the invention that are especially useful in the laundering of coloured fabrics are prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10.0 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme | 0.10 | 0.05 |
| Silicate | 2.5 | — |
| Sulfate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-Ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy-duty liquid fabric cleaning compositions in accordance with the invention may be prepared as follows:

| | | |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme | 0.10 | 0.05 |
| Coco-alkyl dimethyl Hydroxy ethyl ammonium Chloride | — | 3.0 |
| Smectite clay | — | 5.0 |
| PVP | 2.0 | — |
| Water/Minors | Up to 100% | |

Powder Automatic Dish Wash Composition I

| | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetra acetyl ethylene diamine (TAED) | 1-4% |
| Sodium sulphate | 5-33% |
| Enzymes | 0.0001-0.1% |

Powder Automatic Dish Wash Composition II

| | |
|---|---|
| Nonionic surfactant (e.g., alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetra-acetyl ethylene diamine (TAED) | 1-2% |
| Polyacrylate polymer (e.g., maleic acid/acrylic acid copolymer) | 6-25% |
| Enzymes | 0.0001-0.1% |
| Perfume | 0.1-0.5% |
| Water | 5-10 |

Powder Automatic Dish Wash Composition III

| | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetra acetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

Powder Automatic Dish Wash Composition IV

| | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetra-acetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulfate | Balance |

Powder Automatic Dish Wash Composition V

| | |
|---|---|
| Nonionic surfactant | 1-7% |
| Sodium disilicate | 18-30% |
| Trisodium citrate | 10-24% |
| Sodium carbonate | 12-20% |
| Monopersulfate (2 $KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulfate, water | Balance |

Powder and Liquid Dish Wash Composition with Cleaning Surfactant System VI

| | |
|---|---|
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetra acetyl ethylene diamine (TAED) | 0-4% |
| Maleic acid/acrylic acid copolymer | 0-7.5% |
| Sodium sulfate | 0-12.5% |
| Enzymes | 0.0001-0.1% |

Non-Aqueous Liquid Automatic Dishwashing Composition VII

| | |
|---|---|
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycol ethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

Non-Aqueous Liquid Dishwashing Composition VIII

| | |
|---|---|
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher glycols, polyglycols, polyoxides and glycol ethers | Balance |

Thixotropic Liquid Automatic Dishwashing Composition IX

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulfonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decyldiphenyl oxide disulfonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

Liquid Automatic Dishwashing Composition X

| | |
|---|---|
| Alcohol ethoxylate | 0-20% |
| Fatty acid ester sulfonate | 0-30% |
| Sodium dodecyl sulfate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetra acetyl ethylene diamine (TAED) | 0-8% |
| Maleic acid/acrylic acid copolymer | 4-8% |
| Enzymes | 0.0001-0.1% |

Liquid Automatic Dishwashing Composition Containing Protected Bleach Particles XI

| | |
|---|---|
| Sodium silicate | 5-10% |
| Tetra potassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

XII: Automatic dishwashing compositions as described in I, II, III, IV, VI and X, wherein perborate is replaced by percarbonate.

XIII: Automatic dishwashing compositions as described in I-VI, which additionally contain a manganese catalyst. The manganese catalyst may, e.g., be one of the compounds described in "Efficient manganese catalysts for low-temperature bleaching", Nature, (1994), 369, 637-639.

Materials and Methods

Textiles:

Standard textile pieces are obtained from WFK Testgewebe GmbH, Christenfeld 10, D-41379 Brüggen-Bracht, Germany.

Strains:

B. subtilis DN1885 (Diderichsen et al., 1990).

B. lentus 309 and 147 are specific strains of Bacillus lentus, deposited with the NCIB and accorded the accession numbers NCIB 10309 and 10147, and described in U.S. Pat. No. 3,723,250 incorporated by reference herein.

E. coli MC 1000 (M. J. Casadaban and S. N. Cohen (1980); J. Mol. Biol. 138 179-207), was made r⁻, m⁺ by conventional methods and is also described in U.S. patent application Ser. No. 039,298.

Plasmids:

pJS3: E. coli-B. subtilis shuttle vector containing a synthetic gene encoding for subtilase 309 (Described by Jacob Schiødt et al. in Protein and Peptide letters 3:39-44 (1996)).

pSX222: B. subtilis expression vector (described in WO 96/34946).

General Molecular Biology Methods:

Unless otherwise mentioned the DNA manipulations and transformations are performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations are used according to the specifications of the suppliers.

Enzymes for DNA Manipulations

Unless otherwise mentioned all enzymes for DNA manipulations, such as e.g. restriction endonucleases, ligases etc., are obtained from New England Biolabs, Inc.

Proteolytic Activity

In the context of this invention proteolytic activity is expressed in Kilo NOVO Protease Units (KNPU). The activity is determined relatively to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novozymes NS, Denmark, which folder is hereby included by reference.

A GU is a Glycine Unit, defined as the proteolytic enzyme activity that, under standard conditions, during a 15 minutes' incubation at 40° C., with N-acetyl casein as substrate, produces an amount of $NH_2$-group equivalent to 1 mmole of glycine.

Enzyme activity can also be measured using the PNA assay, according to reaction with the soluble substrate succinyl-alanine-alanine-proline-phenyl-alanine-para-nitrophenol, which is described in the Journal of American Oil Chemists Society, Rothgeb, T. M., Goodlander, B. D., Garrison, P. H., and Smith, L. A., (1988).

Fermentation:

Fermentations for the production of subtilase enzymes are performed at 30° C. on a rotary shaking table (300 r.p.m.) in 500 ml baffled Erlenmeyer flasks containing 100 ml BPX medium for 5 days.

Consequently in order to make an e.g. 2 liter broth 20 Erlenmeyer flasks are fermented simultaneously.

Media:

| BPX Medium Composition (per liter) | |
| --- | --- |
| Potato starch | 100 g |
| Ground barley | 50 g |
| Soybean flour | 20 g |
| $Na_2HPO_4 \times 12\ H_2O$ | 9 g |
| Pluronic | 0.1 g |
| Sodium caseinate | 10 g |

The starch in the medium is liquefied with α-amylase and the medium is sterilized by heating at 120° C. for 45 minutes. After sterilization the pH of the medium is adjusted to 9 by addition of $NaHCO_3$ to 0.1 M.

Example 1

Construction and Expression of Enzyme Variants

Site-Directed Mutagenesis:

Subtilase 309 (Savinase®) site-directed variants of the invention comprising specific insertions/deletions/substitutions are made by traditional cloning of DNA fragments (Sambrook et al., Molecular Cloning: A Laboratory Manual, 2nd Ed., Cold Spring Harbor, 1989) produced by PCR with oligos containing the desired mutations (see below).

The template plasmid DNA may be pJS3 (see below), or an analogue of this containing a variant of Subtilase 309.

Mutations are introduced by oligo directed mutagenesis to the construction of variants.

The Subtilase 309 variants are transformed into E. coli. DNA purified from an over night culture of these transformants is transformed into B. subtilis by restriction endonuclease digestion, purification of DNA fragments, ligation, transformation of B. subtilis. Transformation of B. subtilis is performed as described by Dubnau et al., 1971, J. Mol. Biol. 56, pp. 209-221.

Site-Directed Mutagenesis in Order to Introduce Mutations in a Specific Region:

The overall strategy used to perform site-directed mutagenesis is:

Mutagenic primers (oligonucleotides) are synthesized corresponding to the DNA sequence flanking the sites of mutation, separated by the DNA base pairs defining the insertions/deletions/substitutions.

Subsequently, the resulting mutagenic primers are used in a PCR reaction with the modified plasmid pJS3 (see above). The resulting PCR fragment is purified and extended in a second PCR-reaction, the resulting PCR product is purified and extended in a third PCR-reaction before being digested by endonucleases and cloned into the E. coli-B. subtilis shuttle vector (see below). The PCR reactions are performed under normal conditions.

The plasmid DNA is transformed into E. coli by well-known techniques and one E. coli colony is sequenced to confirm the mutation designed.

The below listed variants are constructed as described above in the parent subtilisin 309 (SEQ ID NO:4), the sequence of which is shown in FIG. 1:

V11{A,R,N,D,C,Q,E,G,H,I,L,K,M,F,S,T,W,Y}, deletion, insertion;
V30{A,R,N,D,C,Q,E,G,H,I,L,K,M,F,P,S,T,W,Y}, deletion, insertion;
L31{R,N,D,Q,E,H,K,M,P,W,Y}, deletion, insertion;
D32{A,R,C,E,G,H,I,L,K,M,F,P,T,W,Y,V}, insertion;
G34{A,R,N,D,C,Q,E,H,I,L,K,M,F,S,T,W,Y,V}, deletion;
G65{A,R,C,H,I,L,K,M,F,T,W,Y,V}, deletion, insertion;
T66{A,R,C,H,I,L,K,M,F,W,Y,V}, deletion, insertion;
H67{A,R,N,Q,G,I,K,M,F,P,S,T,W,Y,V};
V68{R,N,D,Q,E,G,H,I,L,K,F,P,S,T,W,Y}, deletion, insertion;
A69{R,N,D,Q,E,G,H,I,L,K,M,F,P,S,T,W,Y,V}, deletion, insertion;
G83 insertion;
A85{R,N,D,Q,E,G,H,I,L,M,F,S,T,W,Y,V};
L90{A,R,N,D,C,Q,E,G,H,I,K,M,F,P,S,T,W,Y,V}, deletion, insertion;
V95{R,K,F,W,Y}, deletion;
G110 insertion;
V121 insertion;
A122 insertion;
V150{A,R,N,D,Q,E,G,H,I,L,K,M,F,P,S,T,W,Y}, deletion, insertion;
A152{R,N,D,Q,E,H,K,F,P,W,Y,V};
S153{R,N,D,Q,E,G,H,I,L,K,M,F,T,W,Y,V};
G154{A,R,H,I,L,M,F,W,Y,V};
*164{A,R,H,T,W};
*165{R,L,F,W,Y};
*166{W,Y}, insertion;
M175{R,N,D,Q,E,G,H,K,F,P,T,W,Y,V};
V177{R,N,D,Q,E,G,H,I,L,K,M,F,P,S,T,W,Y}, deletion, insertion;
G178{A,R,N,D,C,Q,E,H,I,L,K,M,F,P,S,T,W,Y,V}, deletion, insertion;
T180{A,R,N,D,C,Q,E,G,H,I,L,K,M,F,P,S,W,Y,V}, deletion, insertion;
V199{R,L,K,F,W,Y}, deletion, insertion;
A200{R,I,L,K,M,F,W,Y,V}, deletion, insertion;
P201{A,R,H,I,L,K,M,F,T,W,Y,V}, deletion, insertion;
G202{A,R,C,H,I,L,K,M,F,T,W,Y,V};
S207{A,R,N,C,Q,G,H,I,L,K,M,F,P,T,W,Y,V};
T220 insertion;
A223 insertion;
P225 insertion;
H226 insertion;
V227 insertion;
A228 insertion;
G229 insertion;
A230 insertion;
A231A, insertion;
T253{A,R,N,D,Q,E,G,H,I,L,M,F,S,W,Y,V}, deletion, insertion;
G264{A,R,N,Q,H,I,L,M,F,S,T,W,Y,V}, deletion, insertion;
G266{A,R,N,D,C,Q,E,H,I,L,K,M,F,S,T,W,Y,V}, deletion, insertion.

In order to purify a subtilase variant of the invention, a *B. subtilis* pJS3 expression plasmid comprising a variant of the invention is transformed into a competent *B. subtilis* strain and fermented as described above.

Example 2

Purification of Enzyme Variants

This procedure relates to purification of a 2 liter scale fermentation for the production of the subtilases of the invention in a *Bacillus* host cell.

Approximately 1.6 liter of fermentation broth is centrifuged at 5000 rpm for 35 minutes in 1 liter beakers. The pH of the supernatants is adjusted to 6.5 using 10% acetic acid and filtered on Seitz Supra S100 filter plates.

The filtrates are concentrated to approximately 400 ml using an Amicon CH2A UF unit equipped with an Amicon S1Y10 UF cartridge. The UF concentrate is centrifuged and filtered prior to absorption at room temperature on a Bacitracin affinity column at pH 7. The protease is eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step are combined and applied to a 750 ml Sephadex G25 column (5 cm dia.) equilibrated with a buffer containing 0.01 dimethylglutaric acid, 0.2 M boric acid and 0.002 m calcium chloride adjusted to pH 6.5.

Fractions with proteolytic activity from the Sephadex G25 column are combined and applied to a 150 ml CM Sepharose CL 6B cation exchange column (5 cm dia.) equilibrated with a buffer containing 0.01 M dimethylglutaric acid, 0.2 M boric acid, and 0.002 M calcium chloride adjusted to pH 6.5.

The protease is eluted using a linear gradient of 0-0.1 M sodium chloride in 2 liters of the same buffer (0-0.2 M sodium chloride in case of Subtilisin 147).

In a final purification step protease containing fractions from the CM Sepharose column are combined and concentrated in an Amicon ultrafiltration cell equipped with a GR81PP membrane (from the Danish Sugar Factories Inc.).

The following variants according to the invention were produced and purified according to the above procedure.

BPN' (BASBPN):
I11V,L
L90I,V
M199* (deletion)

Savinase (BLSAVI):
V11I; V11I+144V; V11I+L96LA; S9R+V11I+A15T+T22A; V11I+L96LA+A108C+A138C; V11I+N76D+A194P+A230V; V11I+V84I; V11I+V84I+K251R; V11I+V30I; V11I+V139L; V11I+V30I; V30I; V30I+V84I; V30I+V139L; S9R+A15T+T22A+V30I; V30I+V244R; V30I+K251R; V30I+V139L+Y167A+R170S+A194P+N218S; D32A; V68A; V68A+S106A; V68A,+V139I; V68A,+A158V; V68A+V203A; V68A+V139L; A48T+V68A+P131M; V51A+V68A+S106T+A168G; V51A+V68A+S106T+A168G; N76D+M175ML+A194P+A230V; N76D+M175MI+A194P+A230V;

All these variants exhibited proteolytic activity as indicated above.

Example 3

The "Model Detergent Wash Performance Test"

In order to asses the wash performance of selected subtilase variants in a standard detergent composition, standard washing experiments may be performed using the below experimental conditions:
Detergent: Model detergent
Detergent dosage 4.0 g/l
pH 10.1
Wash time 20 min
Temperature: 30° C.
Water hardness: 15° dH
Enzyme concentration: 10 nm (in the detergent solution)
Test system: 10 ml beakers with a stirring rod Textile/volume: 5 textile pieces (Ø 2.5 cm)/50 ml detergent solution Test material: A suitable textile swatch, such as WFK10N (egg stains)

The composition of the model detergent is as follows:

6.2% LAS (Nansa 80S)
2% Sodium salt of $C_{16}$-$C_{18}$ fatty acid
4% Non-ionic surfactant (Plurafax LF404)
22% Zeolite P
10.5% $Na_2CO_3$
4% $Na_2Si_2O_5$
2% Carboxymethylcellulose (CMC)
6.8% Acrylate liquid CP5 40%
20% Sodium perborate (empirical formula $NaBO_2.H_2O_2$)
0.2% EDTA
21% $Na_2SO_4$
Water (balance)

pH of the detergent solution is adjusted to 10.1 by addition of HCl or NaOH. Water hardness is adjusted to 15° dH by addition of $CaCl_2$ and $MGCl_2$ ($Ca^{2+}$:$Mg^{2+}$=4:1) to the test system. After washing the textile pieces are flushed in tap water and air-dried.

Measurement of the reflectance ($R_{variant}$) on the test material is performed at 460 nm using a Macbeth ColorEye 7000 photometer (Macbeth, Division of Kollmorgen Instruments Corporation, Germany). The measurements are performed in accordance with the manufacturer's protocol.

In order to determine a blank value, a similar wash experiment is performed without addition of enzyme. The subsequent measurement of the reflectance ($R_{blank}$) is performed as described right above.

A reference experiment is then performed as described above, wherein the wash performance of the parent enzyme is tested. The subsequent measurement of the reflectance ($R_{parent}$) is performed as described right above.

The wash performance is evaluated by means of the Performance Factor (P) which is defined in accordance with the below formula:

$$P = (R_{variant} - R_{blank}) - (R_{parent} - R_{blank})$$
$$= R_{variant} - R_{parent}.$$

---

The invention claimed is:

1. A subgroup I-S1 or subgroup IS-2 subtilase variant comprising (a) the alteration X68{N,D,Q,E,G,H,I,L,F,P,S,T,W,Y} and (b) one or more of the following alterations at positions 31, 32, 34, 65, 66, 67, 69, 83, 85, 95, 110, 121, 122, 150, 152, 164, 165, 166, 177, 178, 199, 200, 201, 202, 207, 220, 223, 225, 226, 227, 229, 230, 231, 253, 264 and 266, where each position for alteration is numbered according to the amino acid sequence set forth in SEQ ID NO:3:

X31{R,N,D,Q,E,H,K,M,P,W,Y}, deletion, insertion;
X32{A,R,C,E,G,H,I,L,K,M,F,P,T,W,Y,V}, insertion;
X34{A,R,N,D,C,Q,E,H,I,L,K,M,F,S,T,W,Y,V}, deletion;
X65{A,R,C,H,I,L,K,M,F,T,W,Y,V}, deletion, insertion;
X66{A,R,C,H,I,L,K,M,F,W,Y,V}, deletion, insertion;
X67{A,R,N,Q,G,I,K,M,F,P,S,T,W,Y,V};
X69{R,N,D,Q,E,G,H,I,L,K,M,F,P,S,T,W,Y,V}, deletion, insertion;
X83 insertion;
X85{R,N,D,Q,E,G,H,I,L,M,F,T,W,Y,V};
X95{R,K,F,W,Y}, deletion;
X110 insertion;
X121 insertion;
X122 insertion;
X150{A,R,N,D,Q,E,G,H,I,L,K,M,F,P,S,T,W,Y}, deletion, insertion;
X152{R,N,D,Q,E,H,K,F,P,W,Y,V};
X164{A,R,H,W};
X165{R,F,W,Y};
X166 insertion;
X177{R,N,D,Q,E,G,H,I,L,K,M,F,P,S,T,W,Y}, deletion, insertion;
X178{A,R,N,D,C,Q,E,G,H,I,L,K,M,F,P,S,T,W,Y,V}, deletion, insertion;
X199{R,K,F,W,Y}, deletion, insertion;
X200{R,I,L,K,M,F,W,Y,V}, deletion, insertion;
X201{A,R,H,I,L,K,M,F,T,W,Y,V}, deletion, insertion;
X202{A,R,C,H,I,L,K,M,F,T,W,Y,V};
X207{A,R,N,C,Q,G,H,I,L,K,M,F,P,S,T,W,Y,V};
X220 insertion;
X223 insertion;
X225 insertion;
X226 insertion;
X227 insertion;
X229 insertion;
X230 insertion;
X231 insertion;
X253{A,R,N,D,Q,E,G,H,I,L,M,F,S,W,Y,V}, deletion, insertion;
X264{A,R,N,Q,H,I,L,M,F,S,T,W,Y,V}, deletion, insertion;
X266{A,R,N,D,C,Q,E,H,I,L,K,M,F,S,T,W,Y,V}, deletion, insertion.

2. The variant of claim 1, wherein the sub-group I-S1 subtilase is selected from the group consisting of BASBPN, BSS168, BSSDY and BLSCAR.

3. The variant of claim 1, wherein the sub-group I-S2 subtilase is selected from the group consisting of BLS147, BLSAVI, BAPB92, and BYSYAB.

4. The variant of claim 1, wherein the sub-group I-S2 subtilase is BLSAVI.

5. The variant of claim 4, wherein the variant comprises one or more of the following alterations:
X31{R,N,D,Q,E,H,K,M,P,W,Y};
X32{A,R,C,E,G,H,I,L,K,M,F,P,T,W,Y,V};
X34{A,R,N,D,C,Q,E,H,I,L,K,M,F,S,T,W,Y,V}.

6. The variant of claim 4, wherein the variant comprises one or more of the following alterations:
X65{A,R,C,H,I,L,K,M,F,T,W,Y,V};
X66{A,R,C,H,I,L,K,M,F,W,Y,V};
X67{A,R,N,Q,G,I,K,M,F,P,S,T,W,Y,V};
X69{R,N,D,Q,E,G,H,I,L,K,M,F,P,S,T,W,Y,V}.

7. The variant of claim 4, wherein the variant comprises the following alteration:
X85{R,N,D,Q,E,G,H,I,L,M,F,T,W,Y,V}.

8. The variant of claim 4, wherein the variant comprises the following alteration:
X95{R,K,F,W,Y}.

9. The variant of claim 4, wherein the variant comprises one or more of the following alterations:
X150{A,R,N,D,Q,E,G,H,I,L,K,M,F,P,S,T,W,Y}
X152{R,N,D,Q,E,H,K,F,P,W,Y,V}.

10. The variant of claim 4, wherein the variant comprises X154{A,R,G,H,I,L,M,F,W,Y,V}.

11. The variant of claim 4, wherein the variant comprises one or more of the following alterations:
X164{A,R,H,W};
X165{R,F,W,Y};
X177{R,N,D,Q,E,G,H,I,L,K,M,F,P,S,T,W,Y}.

12. The variant of claim 4, wherein the variant comprises one or more of the following alterations:
X178{A,R,N,D,C,Q,E,G,H,I,L,K,M,F,P,S,T,W,Y,V};
X199{R,K,F,W,Y};
X200{R,I,L,K,M,F,W,Y,V};

X201{A,R,H,I,L,K,M,F,T,W,Y,V};
X202{A,R,C,H I,L,K,M,F,T,W,Y,V}.

13. The variant of claim 4, wherein the variant comprises the following alteration:
X207{A,R,N,C,Q,G,H,I,L,K,M,F,P,S,T,W,Y,V}.

14. The variant of claim 4, wherein the variant comprises X228A.

15. The variant of claim 4, wherein the variant comprises X228 insertion.

16. The variant of claim 4, wherein the variant comprises one or more of the following alterations:
X253{A,R,N,D,Q,E,G,H,I,L,M,F,S,W,Y,V};
X264{A,R,N,Q,H,I,L,M,F,S,T,W,Y,V};
X266{A,R,N,D,C,Q,E,H,I,L,K,M,F,S,T,W,Y,V}.

17. A cleaning or detergent composition comprising a variant of claim 4, and a surfactant.

* * * * *

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Nomenclature example

<400> SEQUENCE: 1

Ala Gly Lys Ala Leu
1               5

<210> SEQ ID NO 2
<211> LENGTH: 4
<212> TYPE: PRT
<213> ORGANISM: Artificial Sequence
<220> FEATURE:
<223> OTHER INFORMATION: Nomenclature example

<400> SEQUENCE: 2

Ala Gly Gly Leu
1

<210> SEQ ID NO 3
<211> LENGTH: 275
<212> TYPE: PRT
<213> ORGANISM: B. amyloliquefaciens (subtilisin BPN')

<400> SEQUENCE: 3

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80
```

```
Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
    130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
    275

<210> SEQ ID NO 4
<211> LENGTH: 269
<212> TYPE: PRT
<213> ORGANISM: Bacillus lentus

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
```

-continued

```
                165                 170                   175
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```